(12) United States Patent
Kim et al.

(10) Patent No.: US 11,854,193 B2
(45) Date of Patent: Dec. 26, 2023

(54) VALIDITY EVALUATION DEVICE FOR CANCER REGION DETECTION

(71) Applicant: JLK INC., Cheongju-si (KR)

(72) Inventors: Won Tae Kim, Suwon-si (KR); Shin Uk Kang, Seoul (KR); Myung Jae Lee, Seoul (KR); Dong Min Kim, Seoul (KR); Jin Seong Jang, Seoul (KR)

(73) Assignee: JLK INC., Cheongju-si (KR)

( * ) Notice: Subject to any disclaimer, the term of this patent is extended or adjusted under 35 U.S.C. 154(b) by 478 days.

(21) Appl. No.: 17/228,664

(22) Filed: Apr. 12, 2021

(65) Prior Publication Data

US 2021/0303933 A1 Sep. 30, 2021

Related U.S. Application Data

(63) Continuation of application No. PCT/KR2019/013395, filed on Oct. 11, 2019.

(30) Foreign Application Priority Data

Oct. 11, 2018 (KR) .................. 10-2018-0121394

(51) Int. Cl.
*G06K 9/00* (2022.01)
*G06T 7/00* (2017.01)
(Continued)

(52) U.S. Cl.
CPC ............ *G06T 7/0012* (2013.01); *A61B 5/055* (2013.01); *G06F 18/214* (2023.01);
(Continued)

(58) Field of Classification Search
CPC ................. G06T 7/0012; G06T 7/0014; G06T 2207/10088; G06T 2207/20076;
(Continued)

(56) References Cited

U.S. PATENT DOCUMENTS

2013/0182931 A1* 7/2013 Fan .................. G06T 7/143
382/131
2018/0240233 A1* 8/2018 Kiraly .................. G06T 7/0012
(Continued)

FOREIGN PATENT DOCUMENTS

KR 10-2013-0082551 A 7/2013
KR 10-1811028 B1 12/2017
(Continued)

OTHER PUBLICATIONS

Automated Prostate Cancer Detection on Multi-parametric MR imaging via Texture Analysis.

*Primary Examiner* — Avinash Yentrapati
(74) *Attorney, Agent, or Firm* — BROADVIEW IP LAW, PC

(57) ABSTRACT

An apparatus for evaluating validity of detection of a cancer region may be provided. The apparatus comprises a parametric magnetic resonance imaging (MRI) provider configured to provide at least one MRI constructed based on different parameters, a first cancer region input unit configured to receive a first cancer region based on the at least one parametric MRI, a cancer region processor including a cancer region detection model for receiving the at least one parametric MRI as input and outputting cancer region information and configured to generate and provide guide information corresponding to an image to be analyzed through the cancer region detection model, a second cancer region input unit configured to receive a second cancer region based on the guide information, and a validity evaluator configured to generate validity evaluation information of the second cancer region, by comparing the first cancer region with the second cancer region based on a pathology image obtained by mapping a region, in which cancer is present, of an extracted body portion.

20 Claims, 15 Drawing Sheets

(51) Int. Cl.
  *G16H 30/40* (2018.01)
  *G06N 20/20* (2019.01)
  *A61B 5/055* (2006.01)
  *G06F 18/21* (2023.01)
  *G06F 18/214* (2023.01)
  *G06V 10/25* (2022.01)
  *G06V 10/82* (2022.01)
  *G06V 10/44* (2022.01)
  *G06V 10/22* (2022.01)

(52) U.S. Cl.
  CPC .......... *G06F 18/217* (2023.01); *G06N 20/20* (2019.01); *G06T 7/0014* (2013.01); *G06V 10/235* (2022.01); *G06V 10/25* (2022.01); *G06V 10/454* (2022.01); *G06V 10/82* (2022.01); *G16H 30/40* (2018.01); *G06T 2207/10088* (2013.01); *G06T 2207/20076* (2013.01); *G06T 2207/20081* (2013.01); *G06V 2201/03* (2022.01)

(58) Field of Classification Search
  CPC .......... G06T 2207/20081; G16H 30/40; G06N 20/20; G06V 10/25; G06V 10/454; G06V 10/235; G06V 10/82; G06V 2201/03; G06F 18/217; G06F 18/214; A61B 5/055
  See application file for complete search history.

(56) References Cited

U.S. PATENT DOCUMENTS

2019/0370965 A1* 12/2019 Lay .................. G06N 20/00
2021/0041518 A1*  2/2021 Okuda ............... G06T 7/0016

FOREIGN PATENT DOCUMENTS

| KR | 10-2018-0040287 A | 4/2018 |
| KR | 10-2018-0082817 A | 7/2018 |
| KR | 10-1996475 B1 | 6/2019 |

\* cited by examiner

VALIDITY EVALUATION DEVICE FOR CANCER REGION DETECTION

TECHNICAL FIELD

The present disclosure relates to cancer region detection technology, and, more particularly, to a method and apparatus for evaluating validity of a cancer region detected based on image information analysis.

BACKGROUND ART

Deep learning is to learn a very large amount of data to select an answer with highest probability based on the learning result when new data is input. Since such deep learning may adaptively operate according to an image and characteristic factors are automatically found in a process of learning a model based on data, there are increasing attempts to utilize deep learning in an artificial intelligence field in recent years.

On the other hand, in conventional image analysis technology using deep learning in relation to image recognition, a local feature is extracted for each region using convolutional neural network (CNN) technique and max pooling technique and an image is recognized based on the local feature. However, this method has a problem in that an accurate recognition result is not provided with respect to an image which has different content but has a similar local information form.

Meanwhile, various images, that is, parametric MRI, may be reconstructed by applying various parameters to an image of a body of a user or patient using magnetic resonance imaging (MRI). Such parametric MRI may be used as an important factor indicating body change or disease.

However, the condition of the user or patient for a specific disease may appear in various ways and the disease may also have various characteristics or forms. Accordingly, it is difficult to formalize a correlation between information indicated by parametric MRI and body change or disease.

In consideration of this, a relationship between various parametric MRI and particular diseases may be learned based on the global context and local characteristics of an image, and a region where cancer is expected to occur may be detected using a deep learning model built by learning.

Furthermore, in order to increase reliability of a cancer region detected based on a deep learning model, it is necessary to determine whether a cancer region detected based on the deep learning model coincides with an actual cancer region.

DISCLOSURE

Technical Problem

An object of the present disclosure is to provide a method and apparatus for evaluating validity of a cancer region detected based on a deep learning model.

Another object of the present disclosure is to provide a method and apparatus for quantitatively evaluating a degree of coincidence between a cancer region based on a deep learning model and an actual cancer region.

The technical problems solved by the present disclosure are not limited to the above technical problems and other technical problems which are not described herein will become apparent to those skilled in the art from the following description.

Technical Solution

According to an aspect of the present disclosure, an apparatus for evaluating validity of detection of a cancer region may be provided. The apparatus may comprise a parametric magnetic resonance imaging (MRI) provider configured to provide at least one MRI constructed based on different parameters, a first cancer region input unit configured to receive a first cancer region based on the at least one parametric MRI, a cancer region processor including a cancer region detection model for receiving the at least one parametric MRI as input and outputting cancer region information and configured to generate and provide guide information corresponding to an image to be analyzed through the cancer region detection model, a second cancer region input unit configured to receive a second cancer region based on the guide information, and a validity evaluator configured to generate validity evaluation information of the second cancer region, by comparing the first cancer region with the second cancer region based on a pathology image obtained by mapping a region, in which cancer is present, of an extracted body portion.

According to another aspect of the present disclosure, method of evaluating validity of detection of a cancer region may be provided. The method may comprise providing at least one parametric magnetic resonance imaging (MRI) constructed based on different parameters, receiving a first cancer region based on the at least one parametric MRI, building a cancer region detection model for receiving the at least one parametric MRI as input and outputting cancer region information, providing guide information corresponding to an image to be analyzed through the cancer region detection model, receiving a second cancer region based on the guide information, and generating validity evaluation information of the second cancer region by comparing the first cancer region with the second cancer region based on a pathology image obtained by mapping a region, in which cancer is present, of an extracted body portion.

The features briefly summarized above with respect to the present disclosure are merely exemplary aspects of the detailed description below of the present disclosure, and do not limit the scope of the present disclosure.

Effects of Invention

According to the present disclosure, it is possible to provide a method and apparatus for evaluating validity of a cancer region detected based on a deep learning model.

According to the present disclosure, it is possible to provide a method and apparatus for quantitatively evaluating a degree of coincidence between a cancer region based on a deep learning model and an actual cancer region.

According to the present disclosure, it is possible to provide a method and apparatus for evaluating validity of a cancer region checked based on a deep learning model, based on a degree of coincidence between a cancer region set by referring to a deep learning model based cancer region and an actual cancer region and a degree of coincidence between a cancer region set without referring to the deep learning model based cancer region and the actual cancer region.

It will be appreciated by persons skilled in the art that that the effects that can be achieved through the present disclosure are not limited to what has been particularly described hereinabove and other advantages of the present disclosure will be more clearly understood from the detailed description.

MODE FOR INVENTION

Figure 1:
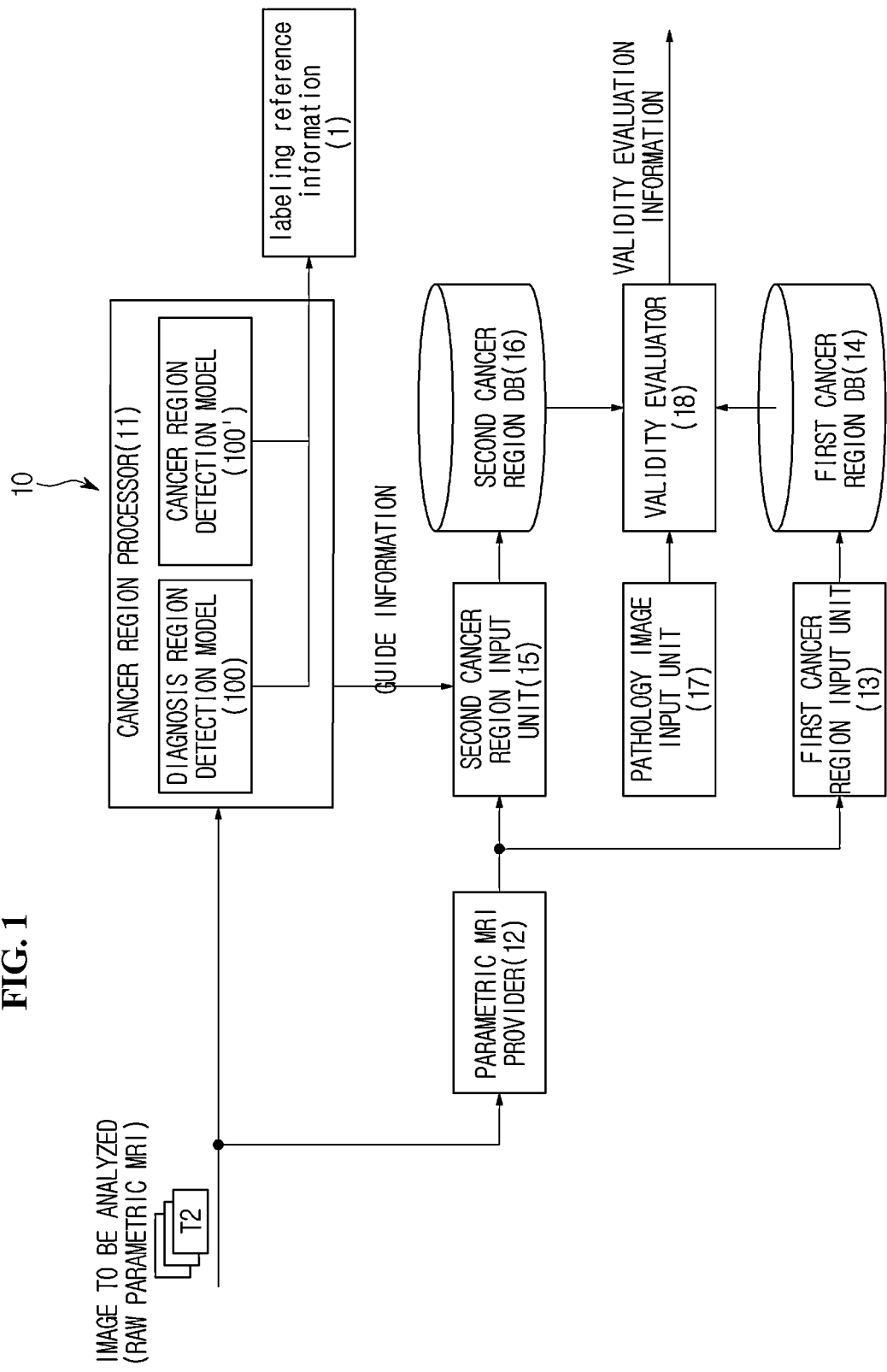
FIG. 1 is a block diagram illustrating the configuration of an apparatus for evaluating validity of detection of a cancer region according to an embodiment of the present disclosure.

Hereinbelow, exemplary embodiments of the present disclosure will be described in detail with reference to the accompanying drawings such that the present disclosure can be easily embodied by one of ordinary skill in the art to which this invention belongs. However, the present disclosure may be variously embodied, without being limited to the exemplary embodiments.

In the description of the present disclosure, the detailed descriptions of known constitutions or functions thereof may be omitted if they make the gist of the present disclosure unclear. Also, portions that are not related to the present disclosure are omitted in the drawings, and like reference numerals designate like elements.

In the present disclosure, when an element is referred to as being "coupled to", "combined with", or "connected to" another element, it may be connected directly to, combined directly with, or coupled directly to another element or be connected to, combined directly with, or coupled to another element, having the other element intervening therebetween. Also, it should be understood that when a component "includes" or "has" an element, unless there is another opposite description thereto, the component does not exclude another element but may further include the other element.

In the present disclosure, the terms "first", "second", etc. are only used to distinguish one element, from another element. Unless specifically stated otherwise, the terms "first", "second", etc. do not denote an order or importance. Therefore, a first element of an embodiment could be termed a second element of another embodiment without departing from the scope of the present disclosure. Similarly, a second element of an embodiment could also be termed a first element of another embodiment.

In the present disclosure, components that are distinguished from each other to clearly describe each feature do not necessarily denote that the components are separated. That is, a plurality of components may be integrated into one hardware or software unit, or one component may be distributed into a plurality of hardware or software units. Accordingly, even if not mentioned, the integrated or distributed embodiments are included in the scope of the present disclosure.

In the present disclosure, components described in various embodiments do not denote essential components, and some of the components may be optional. Accordingly, an embodiment that includes a subset of components described in another embodiment is included in the scope of the present disclosure. Also, an embodiment that includes the components described in the various embodiments and additional other components are included in the scope of the present disclosure.

First, an apparatus for evaluating validity of detection of a cancer region according to an embodiment of the present disclosure evaluates validity of a cancer region input by a user. In particular, according to an embodiment of the present disclosure, the apparatus for evaluating validity of detection of the cancer region provides an environment in which a user (such as an expert or a doctor) is capable of inputting a first cancer region by referring to parametric MRI and an environment capable of inputting a second cancer region by referring to guide information provided by a cancer region detection model built through deep learning based training. In addition, the apparatus for evaluating validity of detection of the cancer region according to an embodiment of the present disclosure is provided to perform an evaluation for the second cancer region.

Hereinafter, the apparatus for evaluating validity of detection of the cancer region according to the embodiment of the present disclosure will be described with reference to the accompanying drawings.

FIG. 1 is a block diagram illustrating the configuration of an apparatus for evaluating validity of detection of a cancer region according to an embodiment of the present disclosure.

Referring to FIG. 1, the apparatus 10 for evaluating validity of detection of the cancer region according to the embodiment of the present disclosure may include a cancer region processor 11, a parametric MRI provider 12, a first cancer region input unit 13, a second cancer region input unit 15, a pathology image input unit 17 and a validity evaluator 18.

The cancer region processor 11 may include a diagnosis region detection model 100 and a cancer region detection model 100' built by a cancer region learning apparatus 1.

Upon receiving raw parametric MRI, the cancer region processor 11 may detect parametric MRI of a diagnosis region using the diagnosis region detection model 100 and check information on a cancer region (hereinafter referred to as "cancer region information") through the cancer region detection model 100'. In addition, the cancer region processor 11 may generate guide information using the cancer region information.

In addition, the cancer region processor 11 may provide the guide information to the second cancer region input unit 15.

Figure 2A:
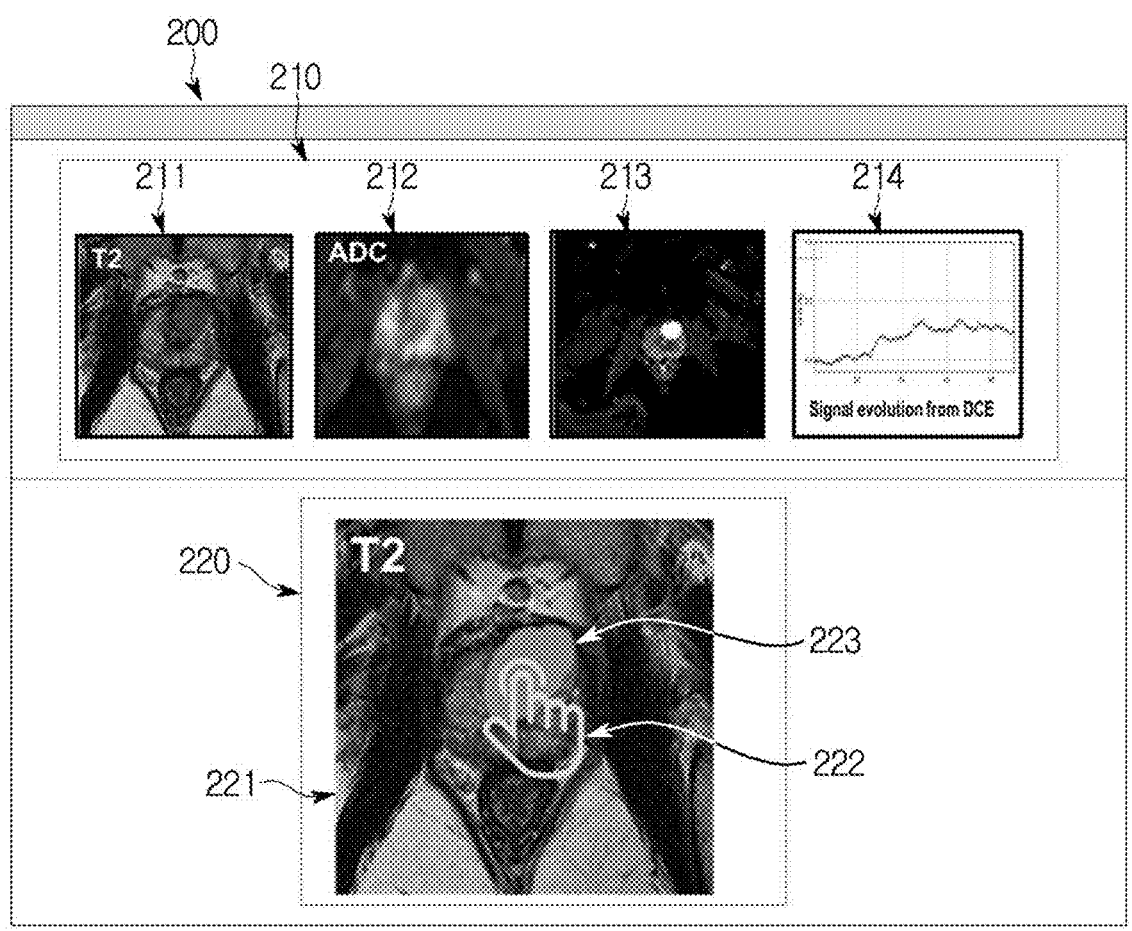
FIGS. 2a and 2b are views illustrating examples of a screen output by the apparatus for evaluating validity of detection of the cancer region according to the embodiment of the present disclosure.

The parametric MRI provider 12 may provide at least one parametric MRI such that a user (such as an expert or a doctor) sets a first cancer region while referring to at least parametric MRI. In addition, the cancer region input unit 13 may provide a screen 200 including a parametric MRI display portion 210 (see FIG. 2*a*) for displaying at least parametric MRI and a first input interface 220 capable of inputting a first cancer region.

For example, the parametric MRI display portion 210 may include display portions 211, 212, 213 and 214 for displaying at least one of a T1 (T1-weighted) image, a T2 (T2-weighted) image, a T2*(T2 star) image, an apparent diffusion coefficients (ADC) image, a fluid attenuated inversion recovery (FLAIR) image, a short TI inversion recovery (STIR) image or a perfusion weighted image (PWI).

In addition, the first input interface 220 may include an image display portion 221 for displaying a T2 image and a predetermined indicator 222 which may be connected through an external input device such as a mouse device, a digitizer device or a touchscreen device and is output in a region designated by an external input device. In addition, the first input interface 220 may set a predetermined region selected through the indicator 222 as a cancer region, and include a first cancer region indicator 223 for displaying the region set as the cancer region.

Although the image display portion 221 displays the T2 image in the embodiment of the present disclosure, the present disclosure does not limit the image displayed by the image display portion 221. The image displayed by the image display portion 221 may be variously changed in correspondence with the diagnosis region or the cancer region.

In addition, the cancer region input unit 13 may store and manage the first cancer region input through the first input interface 220 in a first cancer region DB 14.

Figure 2B:
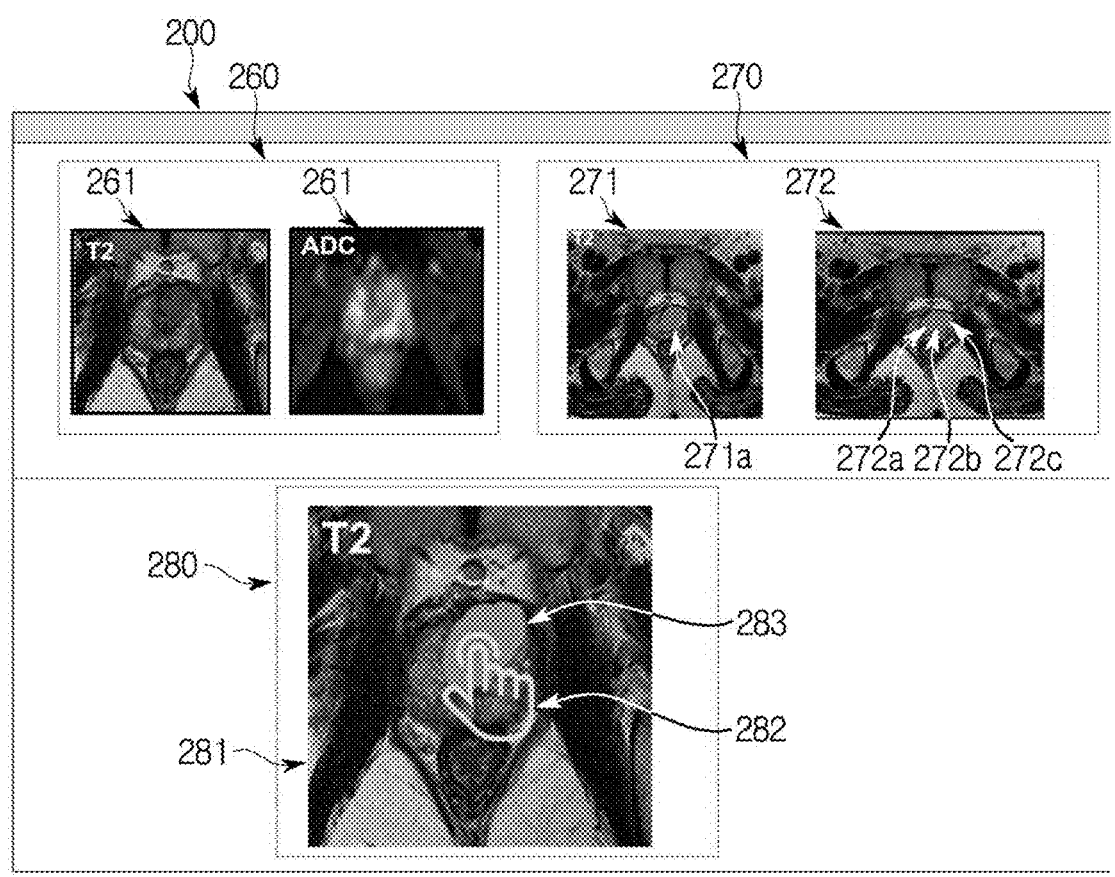

The second cancer region input unit 15 may provide a screen 250 including a parametric MRI display portion 260 (see FIG. 2*b*) for displaying at least one parametric MRI, a guide information display portion 270 for displaying guide information provided by the cancer region processor 11, and a second input interface 280 capable of inputting a second cancer region.

For example, the parametric MRI display portion 260 may include at least one display portion 261 and 262 for displaying at least one of a T1 (T1-weighted) image, a T2 (T2-weighted) image, a T2*(T2 star) image, an apparent diffusion coefficients (ADC) image, a fluid attenuated inversion recovery (FLAIR) image, a short TI inversion recovery (STIR) image or a perfusion weighted image (PWI).

For example, the cancer region processor 11 may set a cancer candidate region through feature region analysis included in at least one parametric MRI and context analysis of a feature region, and generate guide information including the set candidate region. In response to this, the guide information display portion 270 may construct and display guide information including a cancer candidate region 271*a*.

As another example, the cancer region processor 11 may set a predetermined threshold value, set, as a cancer candidate point, a region in which a probability value for a feature region detected as a cancer region exceeds the predetermined threshold value, and generate guide information including the set candidate point. In response to this, the guide information display portion 270 may construct and display a guide image 272 including candidate points 272*a*, 272*b* and 272*c*.

The second input interface 280 provides an environment in which the user is capable of inputting the cancer region similarly to the first input interface, and may include an image display portion 281 for displaying a T2 image, a predetermined indicator 282 output in a region designated by an external input device, and a second cancer region indicator 283 for setting and displaying a predetermined region selected through the indicator 282 as a cancer region.

Although the T2 image is displayed by the image display portion 281 in the example of the present disclosure, the present disclosure does not limit the image displayed by the image display portion 281. The image displayed by the image display portion 281 may be variously changed in correspondence with the diagnosis region or the cancer region.

In addition, the second cancer region input unit 15 may store and manage the second cancer region input through the second input interface 280 in a second cancer region DB 16.

A diagnosis region (e.g., a prostate region) of a user (or a patient) may be extracted through surgery and a pathology image showing a region, in which a cancer tissues are present, in the extracted diagnosis region may be constructed. In consideration of this, the pathology image input unit 17 may provide an environment capable of receiving a pathology image, and display the received pathology image through a display. For example, the pathology image may include an image in which a pathology map of a region, in which cancer is present, of the extracted diagnosis region is constructed in the form of an image.

The pathology image input unit 17 may provide the pathology image to the validity evaluator 18. The validity evaluator 18 may generate validity evaluation information of the second cancer region, by comparing the first cancer region with the second cancer region based on the pathology image.

Figure 3A:
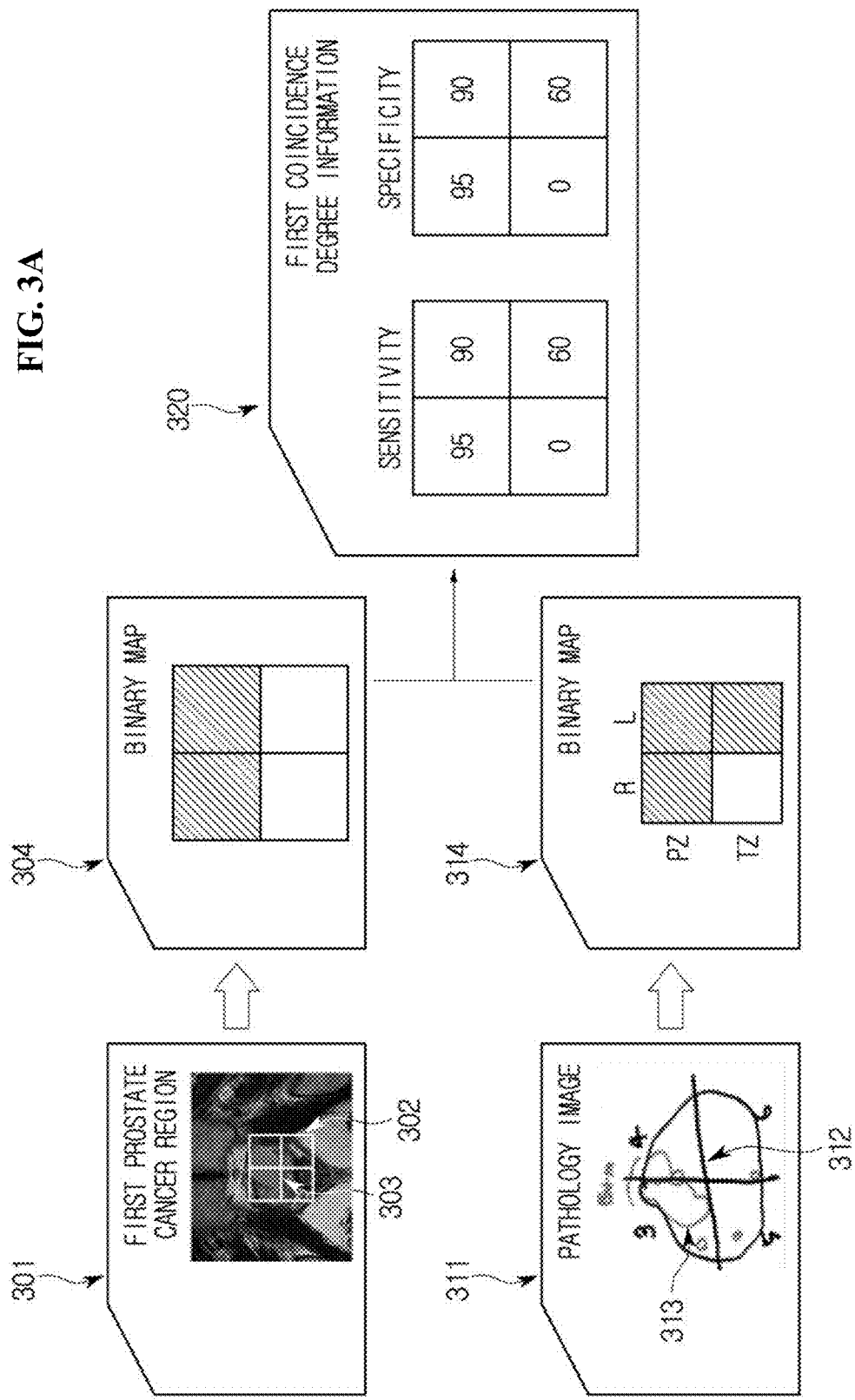
FIGS. 3a to 3c are views illustrating operation of generating validity evaluation information based on information on a degree of coincidence by the apparatus for evaluating validity of detection of the cancer region according to the embodiment of the present disclosure.

For example, the validity evaluator 18 may divide a region, in which a prostate is located, in a predetermined size unit 302 (see FIG. 3*a*), and construct a first binary map 304 for a predetermined unit, in which the first cancer region 303 is present, in the region in which the prostate is located.

In addition, the validity evaluator 18 may divide the pathology image 311 in a predetermined size unit (312), and construct a pathology binary map 314 for a predetermined unit, in which the first cancer region 313 is present, in the region in which the prostate is located.

In addition, the validity evaluator 18 may check first coincidence degree information 320 of the first binary map 304 based on the pathology binary map 314. The first coincidence degree information 320 may be information numerically indicating a degree of similarity between corresponding unit regions of the pathology binary map 314 and the first binary map 304. Further, the first coincidence degree information 320 may include sensitivity information and specificity information of the unit region.

Figure 3B:
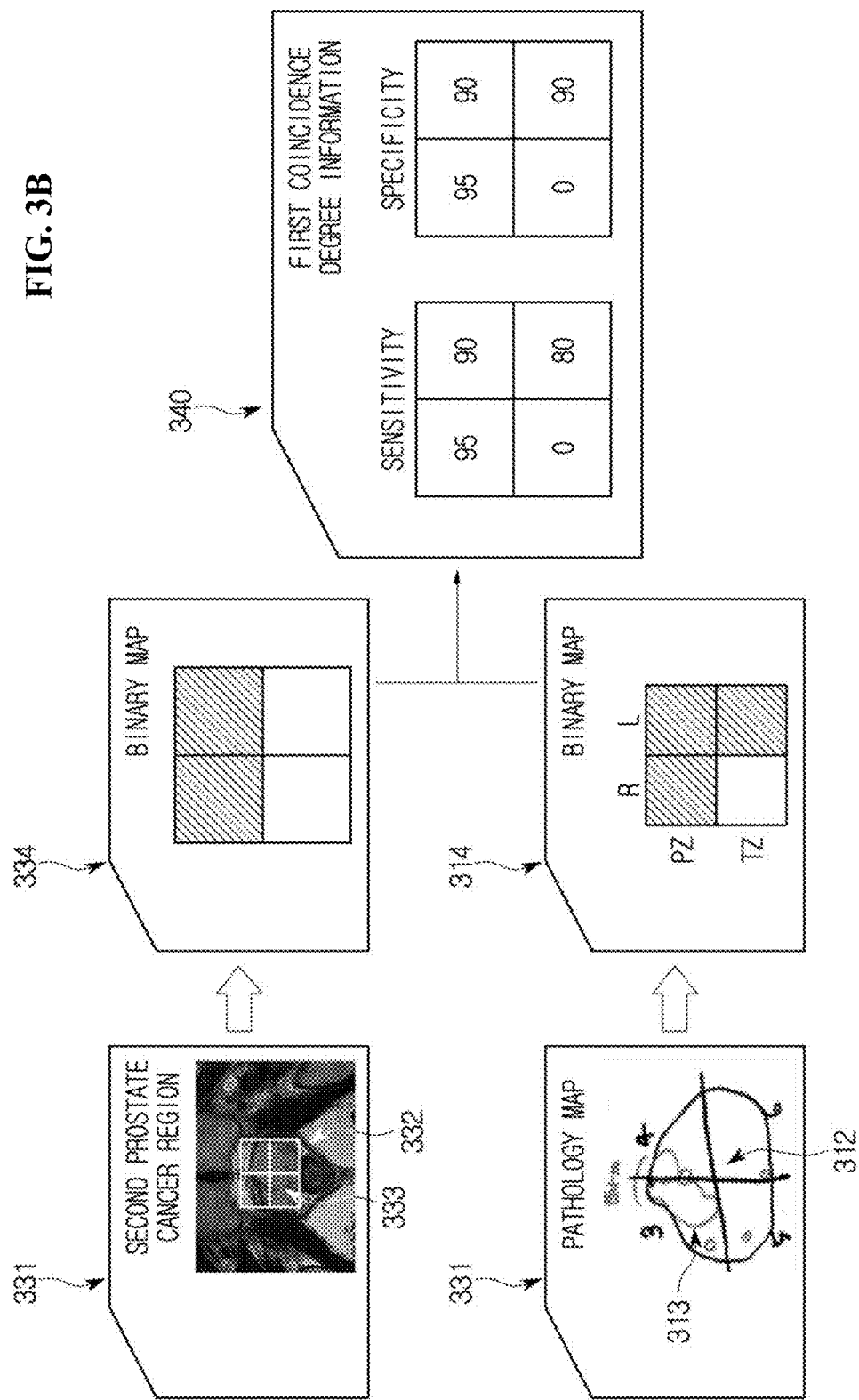

Similarly, the validity evaluator 18 may divide a region, in which the prostate is located, in a predetermined size unit 332 (see FIG. 3*b*), and construct a second binary map 334 for a predetermined unit, in which the second cancer region 333 is present, in the region in which the prostate is located. In addition, the validity evaluator 18 may check second coincidence degree information 340 of the second binary map 334 based on the pathology binary map 314. The second coincidence degree information 340 may be information numerically indicating a degree of similarity between corresponding unit regions of the pathology binary map 314 and the second binary map 334. Further, the second coincidence degree information 340 may include sensitivity information and specificity information of the unit region.

Figure 3C:
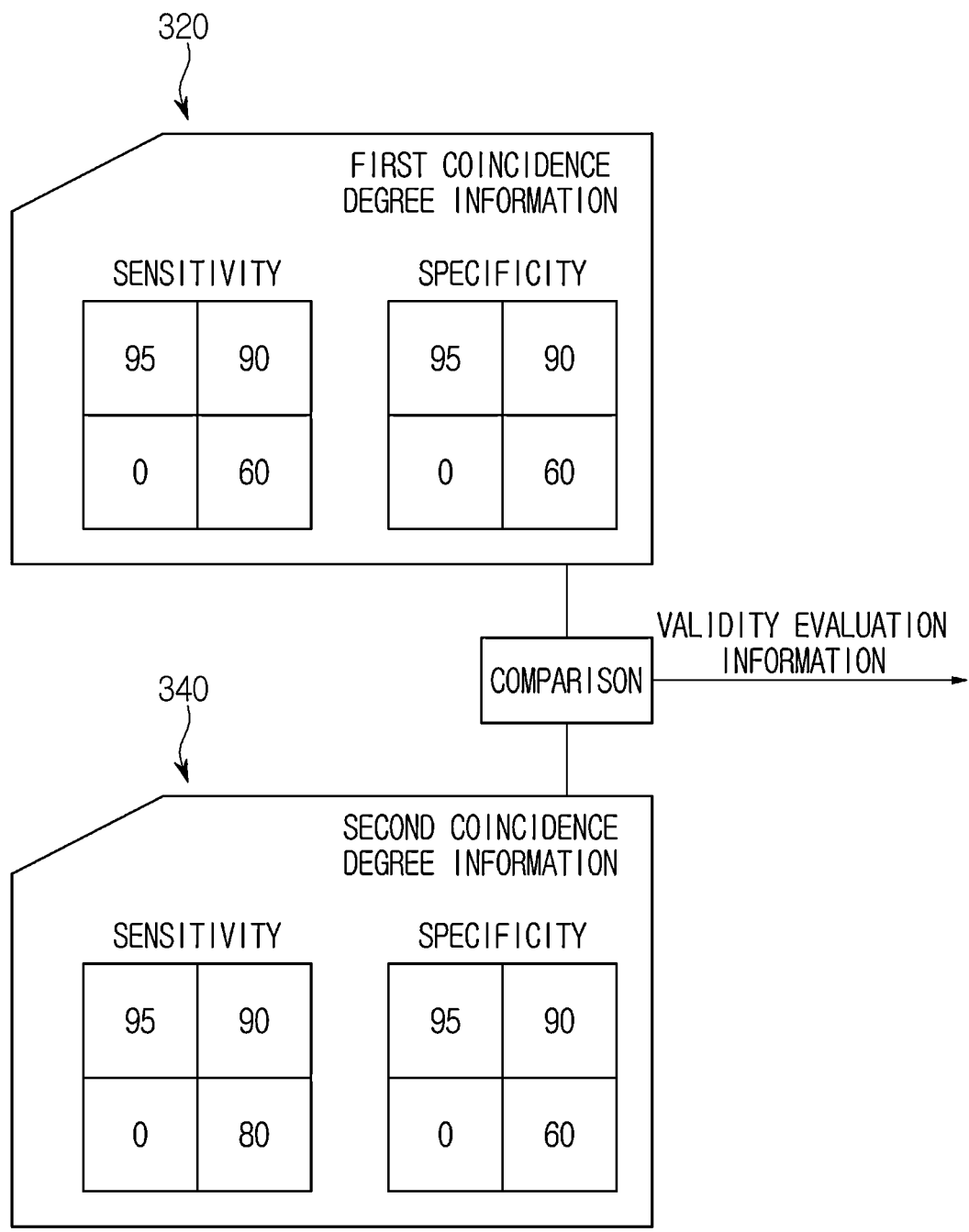

In addition, the validity evaluator 18 may calculate and output validity evaluation information, by comparing the first coincidence degree information 320 with the second coincidence degree information 340 (see FIG. 3c). For example, the validity evaluator 18 may compare the first coincidence degree information 320 with the second coincidence degree information 340, determine that the second cancer region is valid when the second coincidence degree information 340 has a relatively higher value than the first coincidence degree information 320, and determine that the second cancer region is not valid when the second coincidence degree information 340 has the same value as or a relatively lower value than the first coincidence degree information 320.

The second cancer region is a region with a high probability of a cancer region, which is designated by the user (such as the expert or the doctor) based on the guide information provided by the cancer region processor 11. Accordingly, when the validity evaluation information indicates that the second cancer region is valid, the cancer region processor 11 may be recognized as a device which may be effectively used to determine the region where cancer is present.

If there is no difference in input time between the first cancer region and the second cancer region, the user (such as the expert or the doctor) may input the first cancer region (or the second cancer region) and then input the second cancer region (or the first cancer region) in a state in which the first cancer region (or the second cancer region) input thereby is recognized. In this way, when the user (such as the expert or the doctor) inputs the second cancer region (or the first cancer region) in a state in which the first cancer region (or the second cancer region) input thereby is recognized, the second cancer region (or the first cancer region) may be input based on the will of the user (such as the expert or the doctor). When the second cancer region (or the first cancer region) is input based on the will of the user (such as the expert or the doctor), the second cancer region (or the first cancer region) may not be accurately input, and it may be difficult to determine validity of the second cancer region (or the first cancer region).

In consideration of the above description, the validity evaluator 18 may control operation of the cancer region input unit 13 and the second cancer region input unit 15. For example, the validity evaluator 18 may activate the second cancer region input unit 15 to receive the second cancer region, such that the second cancer region is preferentially input. In addition, when a predetermined time (e.g., 1 week or 1 month) has elapsed after input of the second cancer region is completed, the cancer region input unit 13 may be activated to receive the first cancer region corresponding to the second cancer region.

Further, although, in the embodiment of the present disclosure, the cancer region processor 11 is included in the apparatus 10 for evaluating validity of detection of the cancer region, the present disclosure is not limited thereto. The apparatus 10 for evaluating validity of detection of the cancer region may provide an environment capable of inputting the cancer region (the second cancer region) using the guide information provided based on the cancer region detection model.

For example, the cancer region processor 11 may be provided as a separate device from the apparatus 10 for evaluating validity of detection of the cancer region, and may be connected with the apparatus 10 for evaluating validity of detection of the cancer region through wired/wireless communication to provide guide information.

As another example, the cancer region processor 11, the second cancer region input unit 15, and the second cancer region DB 16 may be provided as separate devices, and the cancer region (the second cancer region) may be received using the guide information provided based on the cancer region detection model and stored and managed in the second cancer region DB 16. In addition, the device including the cancer region processor 11, the second cancer region input unit 15 and the second cancer region DB 16 may be connected with the apparatus 10 for evaluating validity of detection of the cancer region through wired/wireless communication to provide the second cancer region stored in the second cancer region DB 16 to the validity evaluator 18.

Figure 4:
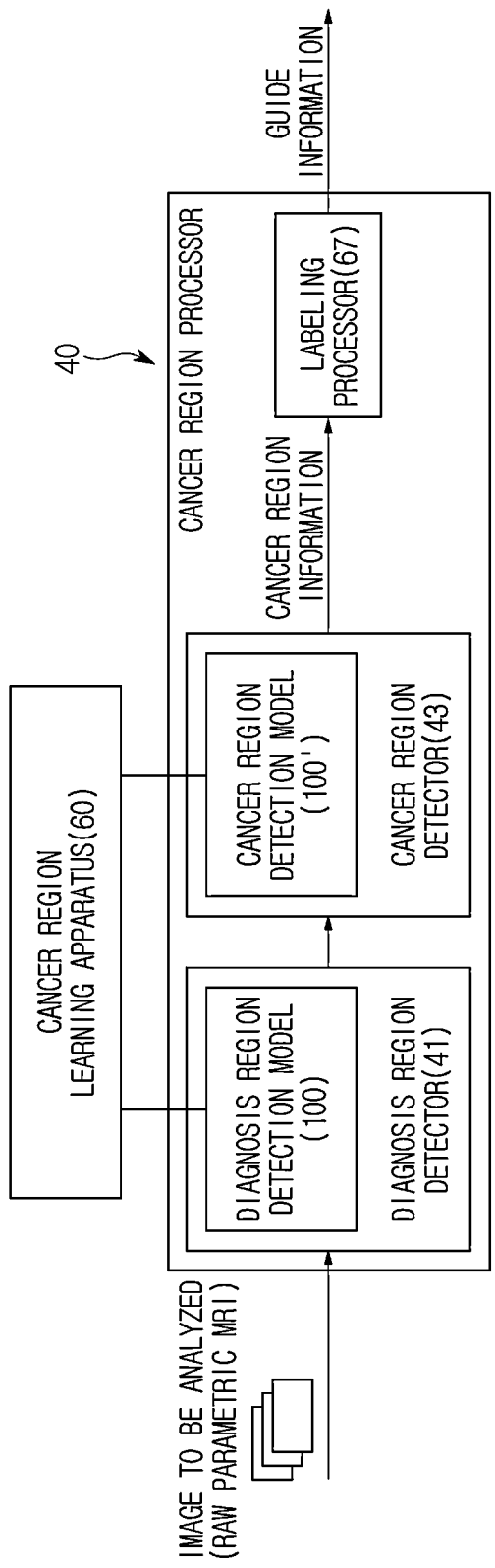
FIG. 4 is a view illustrating the detailed configuration of a cancer region processor shown in FIG. 1.

FIG. 4 is a view illustrating the detailed configuration of the cancer region processor shown in FIG. 1.

Referring to FIG. 4, the cancer region processor according to the embodiment of the present disclosure may generate and provide guide information including the cancer region using a diagnosis region detection model and a cancer region detection model.

Specifically, the cancer region processor 40 may include a diagnosis region detector 41, a cancer region detector 43 and a guide information provider 45.

The diagnosis region detector 41 may include the diagnosis region detection model 100 built by the cancer region learning apparatus 1, and the cancer region detector 43 may include the cancer region detection model 100' built by the cancer region learning apparatus 1.

Figure 5A:
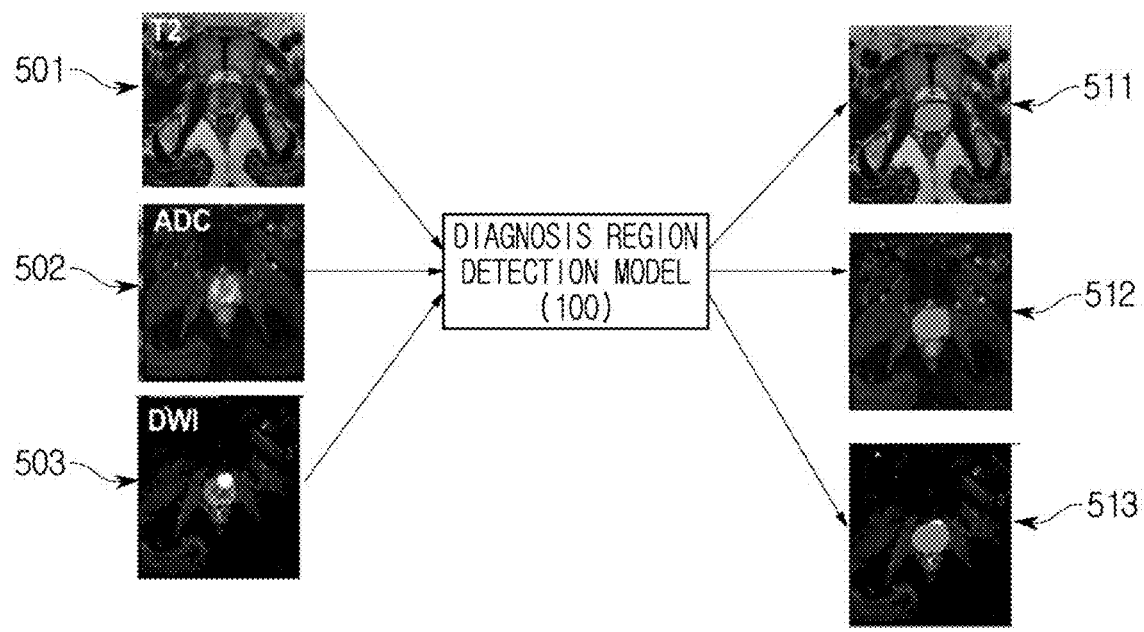
FIGS. 5a to 5c are views illustrating examples of an image processed by the cancer region processor according to an embodiment of the present disclosure.

Upon receiving raw parametric MRI 501, 502 and 503 (see FIG. 5a), the diagnosis region detector 41 may detect and output the parametric MRI 511, 512 and 513 of the diagnosis region using the diagnosis region detection model 100.

In response to this, the cancer region detector 43 may receive the parametric MRI 511, 512 and 513 of the diagnosis region output from the diagnosis region detector 41 and output information on the cancer region (hereinafter referred to as "cancer region information") through the cancer region detection model 100'.

Figure 5B:
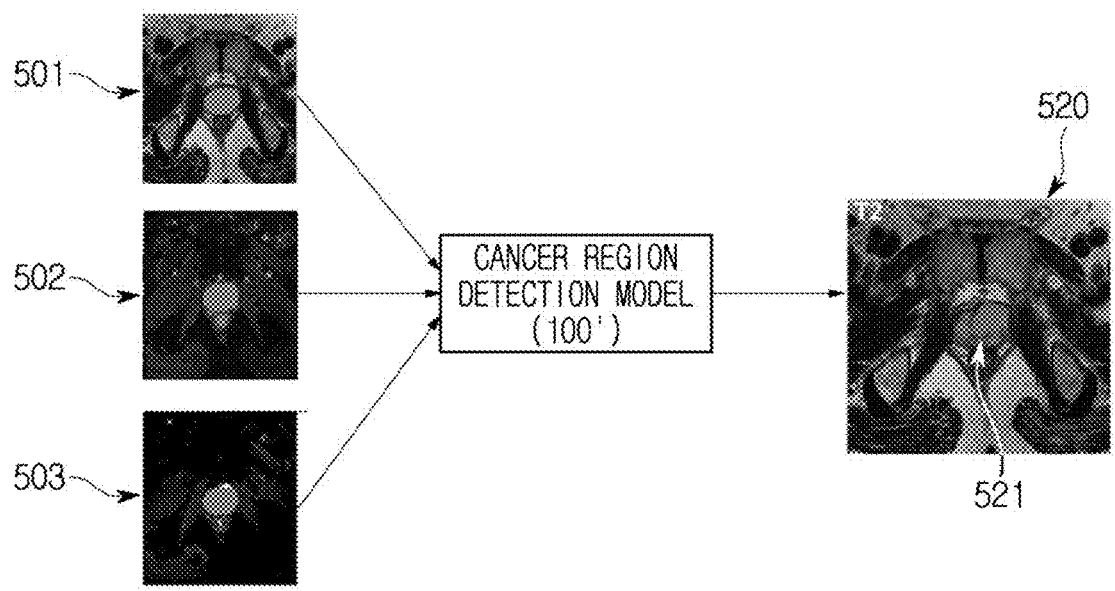

In particular, the cancer region detector 43 may output, as cancer region information, an image 520 in which a region 521 (see FIG. 5b), in which cancer is expected to be present, of the parametric MRI 511, 512 and 513 of the diagnosis region is marked.

The guide information provider 45 may generate guide information using the cancer region information provided by the cancer region detector 43. In addition, the guide information provider 45 may output the generated guide information through a display. For example, the guide information provider 45 may output the image 520, in which the region 521 in which cancer is located is marked, as guide information through the display.

Further, the cancer region detection model 100' may be built through learning that extracts the feature of an image to be analyzed and generates predetermined context information based on the extracted feature, and the context information may be constructed based on a probability value for a feature region included in the image to be analyzed. Based on this, the cancer region detector 43 may construct cancer region information by including the probability value for the feature region detected as the cancer region.

Figure 5C:
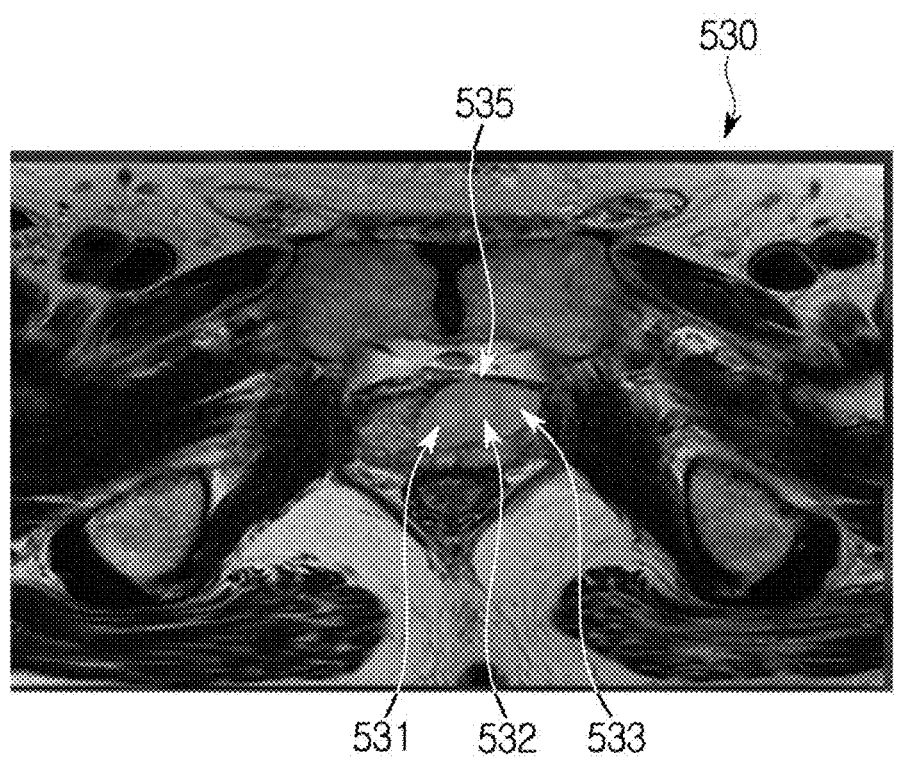

Based on the above description, the guide information may be generated using the probability value for the feature region detected as the cancer region. For example, the cancer region may include a plurality of feature regions having different probability values, and the guide information provider 45 may set a predetermined threshold value, set, as a biopsy candidate point, a region in which the probability value for the feature region detected as the cancer region exceeds the predetermined threshold value, and construct a guide image 530 including the set biopsy candidate points 531, 532 and 533 (see FIG. 5*c*). The probability value for each of the plurality of feature regions may be represented in the form of a probability map and may be displayed to overlap the cancer region as the cancer region information.

In addition, the guide information provider 45 may construct the guide image 530 by marking the cancer region 535 along with the probability map (not shown) or the biopsy candidate points 531, 532 and 533.

The cancer region processor according to the embodiment of the present disclosure may generate and provide guide information including the cancer region using the diagnosis region detection model and the cancer region detection model. The diagnosis region detection model and the cancer region detection model according to the embodiment of the present disclosure may be built by the cancer region learning apparatus according to the embodiment of the present disclosure.

Hereinafter, the cancer region learning apparatus and operation of building the diagnosis region detection model and the cancer region detection model using the same will be described in detail with reference to FIGS. 6 to 8.

Figure 6:
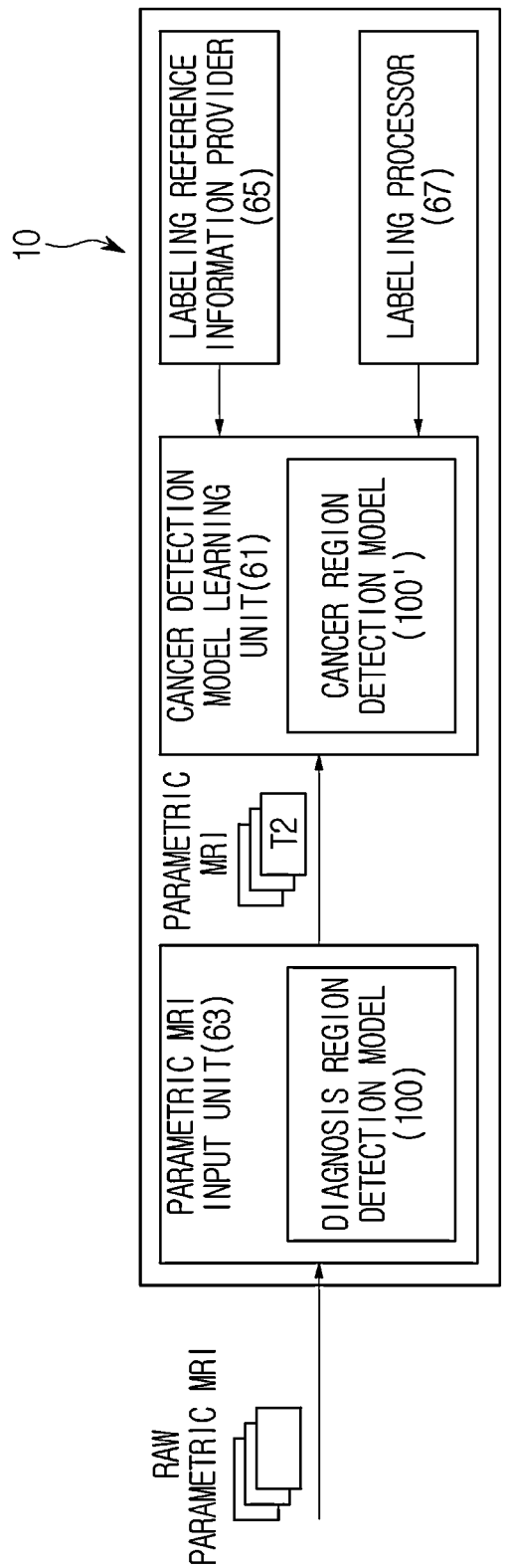
FIG. 6 is a block diagram illustrating the configuration of a cancer region learning apparatus according to an embodiment of the present disclosure.

FIG. 6 is a block diagram illustrating the configuration of a cancer region learning apparatus according to an embodiment of the present disclosure.

Referring to FIG. 6, the cancer region learning apparatus 60 may include a cancer detection model learning unit 61, a parametric MRI input unit 63, a labeling reference information provider 65 and a labeling processor 67.

First, the cancer detection model learning unit 61 may learn the cancer detection model based on the convolutional neural network (CNN) technique or the pooling technique. In particular, the cancer detection model learning unit 61 may receive an image to be analyzed in order to learn the cancer detection model, and perform operation of receiving a particular object or a particular region included in the image to be analyzed, that is, labeling operation.

In addition, the cancer detection model learning unit 61 may learn the cancer detection model, by extracting the feature of the image to be analyzed and generating predetermined context information based on the extracted feature. In addition, the cancer detection model learning unit 61 may build the cancer detection model 600 by repeatedly learning the cancer detection model.

The cancer detection model learning unit 61 may receive an MRI image as the image to be analyzed, and the image to be analyzed may be input by the parametric MRI input unit 63. The parametric MRI input unit 63 may provide an image obtained by capturing a user's body using an MRI apparatus, that is, MRI, to the cancer detection model learning unit 61.

Further, various images may be reconstructed by applying various parameters to the MRI. In the embodiment of the present disclosure, an image reconstructed by applying a predetermined parameter to the MRI is referred to as parametric MRI.

Based on this, the parametric MRI input unit 63 may provide at least one parametric MRI constructed based on different parameters to the cancer detection model learning unit 61. Here, at least one parametric MRI may include a T1 image, a T2 image, a T2*image, an ADC image, a FLAIR image, a STIR image, a PWI, and the like.

Further, the cancer detection model learning unit 61 may learn the cancer detection model for various body organs or diagnosis regions of the user (or the patient), and may selectively use at least one parametric MRI based on the characteristics of each body organ or diagnosis region or the cancer region of each body organ or diagnosis region. To this end, the parametric MRI input unit 63 may selectively input at least one parametric MRI corresponding to the body organ or diagnosis region to the cancer detection model learning unit 61.

For example, when the body organ or the diagnosis region is a prostate region, the parametric MRI input unit 63 may input a T2 image, an ADC image or the like. As another example, when the body organ or the diagnosis region is a liver region, the parametric MRI input unit 63 may input a STIR image, a T1 image, a T1-with-Agents image, a T2 image or the like. As another example, when the body organ or the diagnosis region is a brain region, the parametric MRI input unit 63 may input a T1 image, a T2 image, a FLAIR, or the like.

In addition, the parametric MRI input unit 63 may display the parametric MRI obtained by providing the MRI to the cancer detection model learning unit 61 through a display.

Additionally, the parametric MRI input unit 63 may receive parametric MRI (hereinafter referred to as "raw parametric MRI") based on the MRI obtained by capturing a body in which the user's diagnosis region is located, and detect parametric MRI (hereinafter referred to as "parametric MRI of the diagnosis region") obtained by extracting the diagnosis region from the raw parametric MRI. In addition, the parametric MRI of the diagnosis region may be provided to the cancer detection model learning unit 61 or displayed through a display.

The parametric MRI input unit 63 may extract the parametric MRI of the diagnosis region from the raw parametric MRI based on the CNN technique or the pooling technique. For example, the parametric MRI input unit 63 may build a predetermined learning model through learning which receives the raw parametric MRI as input and outputs the parametric MRI of the diagnosis region. In addition, as the raw parametric MRI is input, the parametric MRI input unit 63 may detect and output the parametric MRI of the diagnosis region.

The labeling reference information provider 65 may provide information contributing to labeling processing of the cancer region.

The pathology image may be constructed by extracting the diagnosis region of the user (or the patient) through surgery and visualizing a region, in which cancer tissues are present, in the extracted diagnosis region. In consideration of this, the labeling reference information provider 65 may provide an environment capable of receiving a pathology image, and display the received pathology image through a display. For example, the pathology image may include a pathology map of a region, in which cancer tissues are present, of the extracted diagnosis region constructed in the form of an image.

Furthermore, since a T2 image, an ADC image or the like is a two-dimensional image, it may be difficult to check cancer tissues present in a region which is not displayed on the image itself. In consideration of this, the labeling reference information provider 65 may check diffusion-weighted imaging (DWI) indicating information on water molecules, which are included in the tissues, diffused in a particular direction in the information included in the MRI, and display the same through a display. Here, the DWI may be received from the MRI apparatus or obtained by processing MRI received from the MRI apparatus.

Similarly, since a T2 image, an ADC image or the like is a two-dimensional image, it may be difficult to check cancer tissues present in a region which is not displayed on the image itself or the characteristics of the tissues. In consideration of this, the labeling reference information provider 65 may check dynamic contrast enhanced (DCE) signal information and build an environment capable of providing the checked DCE signal information. For example, the labeling processor 67 may provide an indicator indicating a region designated by a user while displaying at least one parametric MRI (e.g., a T2 image), and set the region selected by the user as a cancer region. In consideration of this, the labeling reference information provider 65 may check DCE signal information of a region indicated by the indicator generated and displayed by the labeling processor 67 and display the checked DCE signal information through a display.

The labeling reference information provider 65 may display at least one reference information (e.g., a pathology image, DWI, DCE signal information, etc.) through a display.

As another example, the labeling reference information provider may sequentially select and display at least one reference information (e.g., a pathology image, DWI, DCE signal information, etc.). In particular, the labeling reference information provider 65 may sequentially select and display a pathology image, DWI and DCE signal information in conjunction with the labeling processor 67. For example, the labeling reference information provider 65 may display the pathology image along with a T2 image and an ADC image. In addition, in a state in which the pathology image is displayed, as information primarily labeling the cancer region by the labeling processor 67 is input, the labeling reference information provider 65 may display DWI along with the T2 image and the ADC image. In addition, in a state in which DWI is displayed, as information secondarily labeling the cancer region by the labeling processor 67 is input, the labeling reference information provider 65 may check a region indicated by an indicator and check and display DCE signal information corresponding to the region.

Although, in the embodiment of the present disclosure, the labeling reference information provider 65 sequentially provides at least one reference information and at least one reference information is illustrated as a pathology image, DWI, DCE signal information, etc., the present disclosure is not limited thereto and various changes may be made by those skilled in the art. Of course, the order of at least one reference information provided by the labeling reference information provider 65 may also be variously changed.

Further, information which may be used as reference information of labeling (that is, reference information) may be variously changed according to the characteristics of each body organ or diagnosis region or the cancer region present in the body organ or diagnosis region. Accordingly, the labeling reference information provider 65 may selectively provide reference information contributing to labeling process of the cancer region based on the characteristics of each body organ or diagnosis region or the cancer region present in the body organ or diagnosis region.

For example, when the body organ or the diagnosis region is a prostate region, the labeling reference information provider 65 may provide a T1 Contrast image, a T2 Contrast image, PET (Positron Emission Tomography), SPECT (single photon emission computed tomography), DSA (Digital Subtraction Angiography) or the like as reference information. As another example, when the body organ or the diagnosis region is a liver region, the labeling reference information provider 65 may provide a T1 Contrast image, a T2 Contrast image or the like as reference information. As another example, when the body organ or the diagnosis region is a brain region, the labeling reference information provider 65 may provide FDG-PET, SPECT, etc. as reference information.

As described above, the labeling processor 67 may provide an environment capable of performing operation of designating an output value for enabling the cancer detection model learning unit 61 to learn the cancer detection model, that is, labeling, while at least one parametric MRI (e.g., a T2 image) is provided.

Specifically, the labeling processor 67 may provide an interface for outputting at least one parametric MRI (e.g., a T2 image) to a display and receiving a region, in which cancer is present, of the output at least one parametric MRI (e.g., a T2 image), that is, the cancer region. For example, the labeling processor 67 may be connected through an external input device such as a mouse device, a digitizer device or a touchscreen device, to output a predetermined indicator in a region designated by the external input device and to set a region selected through the external input device as a cancer region.

Figure 7:
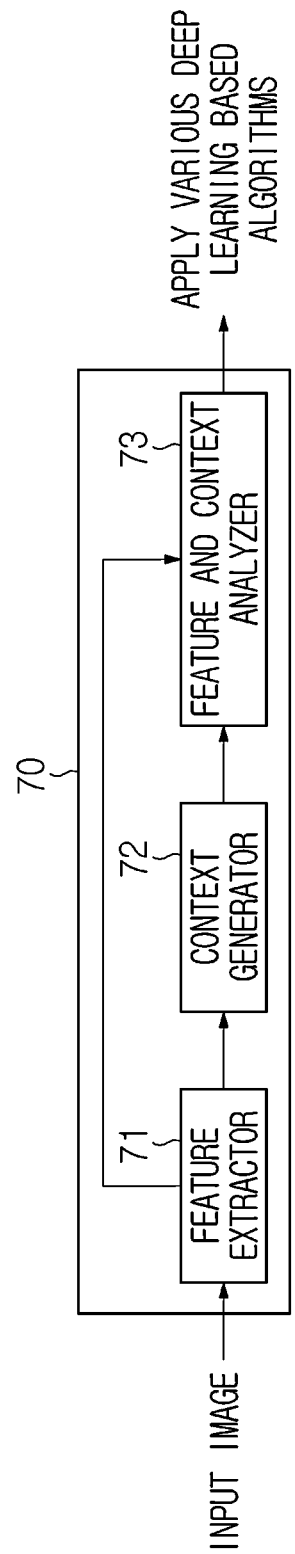
FIG. 7 is a block diagram illustrating the configuration of a cancer detection model learning unit provided in a deep learning model learning apparatus according to an embodiment of the present disclosure.

FIG. 7 is a block diagram illustrating the configuration of a cancer detection model learning unit provided in a cancer region learning apparatus according to an embodiment of the present disclosure.

Referring to FIG. 7, the cancer detection model learning unit 70 may include a feature extractor 71, a context generator 72, and a feature and context analyzer 73. However, only some components necessary to describe the present embodiment are shown and the components included in the cancer detection model learning unit 70 are not limited to the above-described example.

The cancer detection model learning unit 70 may extract the feature of the image to be analyzed, generate context information based on the extracted feature, and analyze the image to be analyzed based on the extracted feature and the generated context information. For example, the cancer detection model learning unit 70 may classify the image or find the location of an object of interest using the extracted feature and the generated context information.

The input image of the cancer detection model learning unit 70 may be at least one parametric MRI. The at least one parametric MRI (e.g., a T2 image, an ADC image or the like) may be a raw image reconstructed from the MRI based on a predetermined parameter or an image in an arbitrary format for storing or transmitting the raw image.

The feature extractor 71 may extract the feature of the image by analyzing the input image. For example, the feature may be a local feature of each region of the image. The feature extractor 71 according to an embodiment may extract the feature of the input image using CNN technique or pooling technique. The pooling technique may include at least one of max pooling technique or average pooling technique. However, the pooling technique described in the present disclosure is not limited to the max pooling technique or the average pooling technique and includes arbitrary technique for obtaining a representative value of an image region having a predetermined size. For example, the representative value used in the pooling technique may be at least one of a variance value, a standard deviation value, a mean value, a most frequent value, a minimum value or a weighted average value, in addition to a maximum value and an average value.

The CNN of the present disclosure may be used to extract "features" such as a border, a line color and the like from input data (image) and may include a plurality of layers. Each layer may receive input data and process the input data, thereby generating output data. The CNN may output, as output data, a feature map generated by performing convolution of the input image or the input feature map with filter kernels. Initial layers of the CNN may operate to extract low-level features such as edges or gradients from input. Next layers of the neural network may gradually extract more complicated features, such as eyes or nose. Detailed operation of the CNN will be described below with reference to FIG. 5.

The CNN may include a pooling layer in which a pooling operation is performed, as well as a convolution layer in which a convolution operation is performed. The pooling technique is used to reduce the spatial size of data in the pooling layer. Specifically, the pooling technique may include max pooling technique for selecting a maximum value in the corresponding region and average pooling technique for selecting an average value of the corresponding region. Generally, the max pooling technique is used in an image recognition field. In the pooling technique, generally, the pooling window size and stride are set to the same value. Here, stride means adjustment of a stride to be moved when applying a filter to input data, that is, a movement stride of the filter. The stride may also be used to adjust the size of the output data. Detailed operation of the pooling technique will be described below with reference to FIG. 8.

The feature extractor 71 according to the embodiment of the present disclosure may apply filtering to the image to be analyzed as pre-processing for extracting the feature of the image to be analyzed. Filtering may include Fast Fourier Transform (FFT), histogram equalization, motion artifact removal or noise removal. However, filtering of the present disclosure is not limited to the methods listed above and may include all types of filtering capable of improving image quality.

The context generator 72 may generate context information of the input image (image to be analyzed) using the feature of the input image extracted from the feature extractor 71. For example, the context information may be a representative value indicating the whole or partial region of the image to be analyzed. In addition, the context information may be global context information of the input image. The context generator 72 according to an embodiment may generate context information by applying the CNN technique or the pooling technique to the feature extracted by the feature extractor 71. The pooling technique may be, for example, average pooling technique.

The feature and context analyzer 73 may analyze the image based on the feature extracted by the feature extractor 71 and the context information generated by the context generator 72. The feature and context analyzer 73 according to an embodiment may classify the input image or find the location of an object of interest included in the input image by concatenating the local feature of each region of the image extracted by the feature extractor 71 and the global context reconstructed by the context generator 72. Since information at a particular two-dimensional position in the input image includes not only local feature information but also global context information, the feature and context analyzer 73 may use this information, thereby performing more accurate recognition or classification with respect to input images which have different actual content but have similar local feature information.

As described above, according to the embodiment of the present disclosure, by using not only the local feature used by the general CNN technique but also the global context information, more accurate and efficient learning and image analysis are possible. In this regard, the present disclosure relates to "deep neural network through context analysis".

Figure 8:
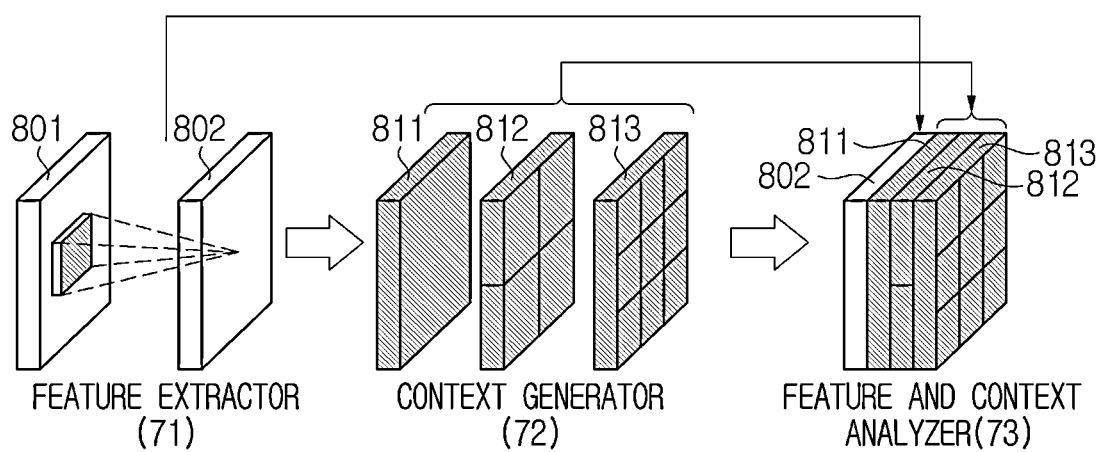
FIG. 8 is a view illustrating a process of generating and analyzing context information of an image according to an embodiment of the present disclosure.

FIG. 8 is a view illustrating a process of generating and analyzing context information of an image according to an embodiment of the present disclosure.

Referring to FIG. 8, the feature extractor 71 may extract a feature from an input image 801 using the input image 801 and generate a feature image 802 including the extracted feature information. The extracted feature may be a feature for a local region of the input image. The input image 801 may include the input image of an image analysis device or a feature map at each layer in a CNN model. In addition, the feature image 802 may include a feature map and/or a feature vector obtained by applying CNN technique and/or pooling technique to the input image 801.

The context generator 72 may generate context information by applying CNN technique and/or pooling technique to the feature image 802 extracted by the feature extractor 71. For example, the context generator 72 may generate context information with various scales, such as the entire image, a ¼ region or a ⅑ region, by variously adjusting pooling stride. Therefore, an entire context information image 811 including context information of the entire image, ¼ context information image 812 including context information of a ¼ image obtained by dividing the entire image into four equal parts and a ⅑ context information image 813 including context information of a ⅑ image obtained by dividing the entire image into nine equal parts.

The feature and context analyzer 73 may more accurately analyze a particular region of the image to be analyzed using both the feature image 802 and the context information images 811, 812 and 813.

For example, when an image including a benign tumor having a form similar to that of prostate cancer is an input image, it is impossible to determine whether the identified object is prostate cancer or benign tumor through the feature image 802 including the local feature extracted by the feature extractor 71. That is, the feature extractor 71 may recognize the shape of the object based on the local feature, but cannot accurately identify and classify the object using only the shape of the object.

The context generator 72 according to the embodiment of the present disclosure may more accurately identify and classify the object, by generating the context information 811, 812 and 813 based on the image to be analyzed or the feature image 802.

The feature and context analyzer 73 according to the embodiment of the present disclosure may identify an object having the shape of prostate cancer or benign tumor as "prostate cancer", by using the context information.

Although, in the embodiment described with reference to FIG. 8, the context information of the entire image, the context information of the ¼ image and the context information of the ⅑ image are generated and used, the size of the image, from which the context information is extracted, is not limited thereto. For example, the context information of the image having a size other than the above-described image size may be generated and used.

Figure 9:
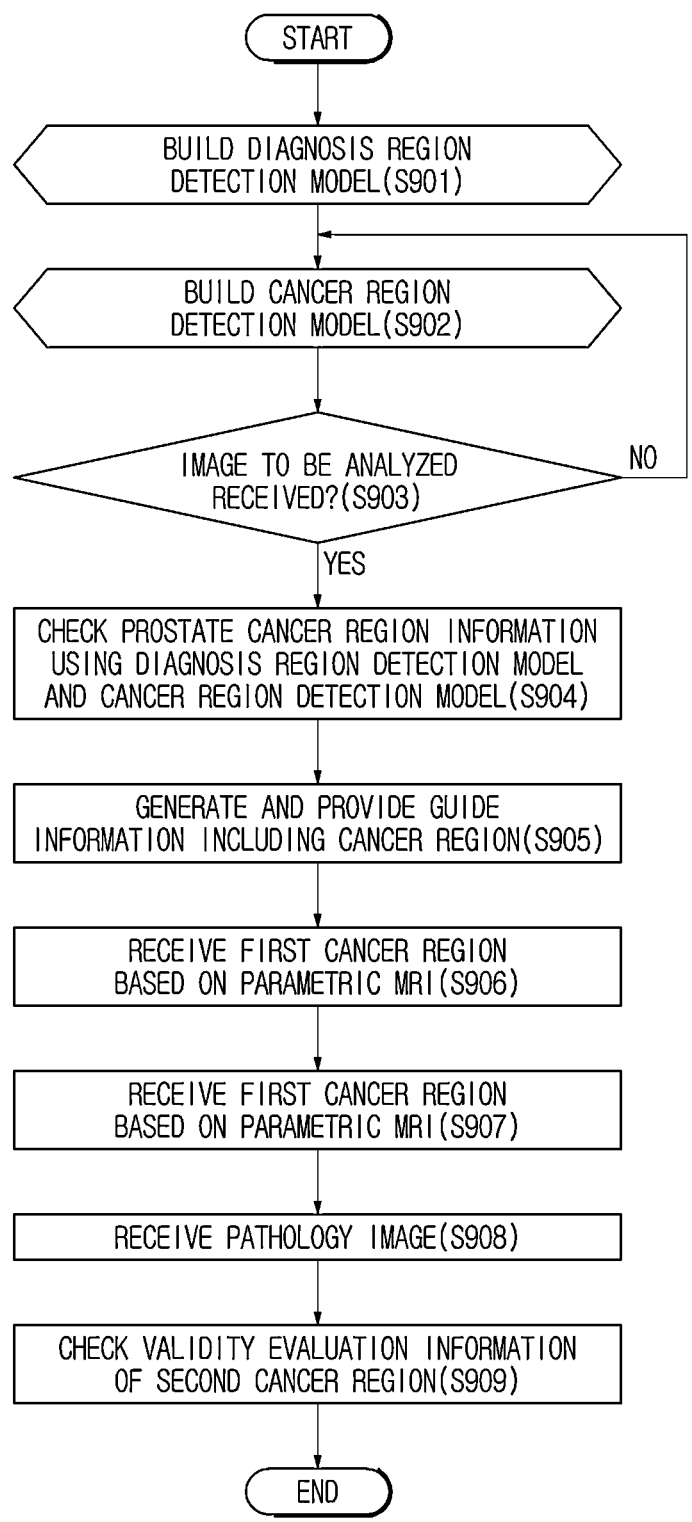
FIG. 9 is a flowchart illustrating a method of evaluating validity of detection of a cancer region according to an embodiment of the present disclosure.

FIG. 9 is a flowchart illustrating a method of evaluating validity of detection of a cancer region according to an embodiment of the present disclosure.

The method of evaluating validity of detection of a cancer region according to the embodiment of the present disclosure may generate and provide guide information based on a diagnosis region detection model and a cancer region detection model, and receive a second cancer region, which has referred to the guide information.

Accordingly, the method of evaluating validity of detection of the cancer region may include step S901 of building a diagnosis region detection model and step S902 of building a cancer region detection model, as operation of preparing the diagnosis region detection model and the cancer region detection model used to generate the guide information.

Step S901 of building the diagnosis region detection model and step S902 of building the cancer region detection model may be performed by the cancer region learning apparatus 60. For detailed operation, refer to the configuration and operation of the cancer region learning apparatus 60 described above.

In step S901, the cancer region learning apparatus may provide at least one parametric MRI. Various images may be reconstructed by applying various parameters to an image obtained by capturing a user's body using an MRI apparatus, that is, MRI. In an embodiment of the present disclosure, an image reconstructed by applying a predetermined parameter to MRI is referred to as parametric MRI. Here, at least one parametric MRI may include a T1 image, a T2 image, a T2*image, an ADC image, a FLAIR image, a STIR image, a PWI, or the like.

Furthermore, the cancer region learning apparatus may learn cancer detection models for various body organs or diagnosis regions of the user (or the patient) and selectively use at least one parametric MRI based on the characteristics of each body organ or diagnosis region or the cancer region of each body organ or diagnosis region. To this end, the cancer region learning apparatus may selectively input at least one parametric MRI corresponding to the body organ or the diagnosis region.

For example, when the body organ or the diagnosis region is a prostate region, the cancer region learning apparatus may input a T2 image, an ADC image or the like. As another example, when the body organ or the diagnosis region is a liver region, the cancer region learning apparatus may input a STIR image, a T1 image, a T1-with-Agents image, a T2 image or the like. As another example, when the body organ or the diagnosis region is a brain region, the cancer region learning apparatus may input a T1 image, a T2 image, a FLAIR, or the like.

Furthermore, at least one parametric MRI may be an image obtained by extracting a region corresponding to a diagnosis region. Specifically, the cancer region learning apparatus may receive raw parametric MRI, and extract parametric MRI obtained by extracting the diagnosis region from the raw parametric MRI, that is, the parametric MRI of the diagnosis region. In addition, the cancer region learning apparatus may provide the parametric MRI of the diagnosis region.

In this case, the cancer region learning apparatus may provide the parametric MRI of the diagnosis region as input for learning of the deep learning model. In addition, the cancer region learning apparatus may construct and provide a screen for providing the parametric MRI of the diagnosis region through a display.

In addition, the cancer region learning apparatus may provide information (hereinafter referred to as "reference information") which may be referenced to designate a region, in which cancer is located, in the parametric MRI of the diagnosis region.

For example, the diagnosis region of the user (or the patient) may be extracted, and the pathology image showing a region, in which cancer tissues are present, in the extracted diagnosis region may be constructed. The cancer region learning apparatus may provide an environment capable of receiving the pathology image. In addition, the cancer region learning apparatus may display the received pathology image through a region of the screen.

MRI may include various parameters. Since a T2 image, an ADC image or the like is a two-dimensional image, it may be difficult to check cancer tissues present in a region which is not displayed on the image itself. Meanwhile, of the image obtained based on MRI, DWI may represent information on water molecules, which is included in tissues, diffused in a particular direction in the information included in the MRI, and thus may represent information which is not displayed on the T2 image or the ADC image. In consideration of this, the cancer region learning apparatus may further display DWI through one region of the screen.

Furthermore, the cancer region learning apparatus may check DCE signal information, and may further display the DCE signal information through one region of the screen. The DCE signal information may be information for checking brightness of a corresponding organ and may be information indicating brightness information of a predetermined region selected from an image obtained based on MRI. Accordingly, the cancer region learning apparatus may check a region selected by the user and display DCE signal information corresponding thereto, through a user interface.

Furthermore, information which may be used as reference information of labeling may be variously changed according to the characteristics of each body organ or diagnosis region or a cancer region of the body organ or diagnosis region. Therefore, the cancer region learning apparatus may selectively provide reference information contributing to labeling processing of the cancer region based on the characteristics of each body organ or diagnosis region or the cancer region of each body organ or diagnosis region.

For example, when the body organ or the diagnosis region is a prostate region, the cancer region learning apparatus may provide a T1 Contrast image, a T2 Contrast image, PET (Positron Emission Tomography), SPECT (single photon emission computed tomography), DSA (Digital Subtraction Angiography) or the like as reference information. As another example, when the body organ or the diagnosis region is a liver region, the cancer region learning apparatus may provide a T1 Contrast image, a T2 Contrast image or the like as reference information. As another example, when the body organ or the diagnosis region is a brain region, the cancer region learning apparatus may provide FDG-PET, SPECT, etc. as reference information.

In addition, the cancer region learning apparatus may provide a user interface capable of performing labeling while displaying the reference information (the pathology image, DWI, DCE signal information or the like).

The user interface may include at least one parametric MRI (e.g., a T2 image). In addition, the user interface may be connected through an external input device such as a mouse device, a digitizer device or a touchscreen device, and include a predetermined indicator output in a region designated by the external input device. In addition, the cancer region learning apparatus may set a predetermined region selected through the indicator as a cancer region, and the user interface may include a labeling indicator for displaying the region set as the cancer region.

When the cancer region is set through the user interface, the cancer region learning apparatus may learn the cancer detection model by receiving the parametric MRI of the diagnosis region as input and outputting the labeled region.

Meanwhile, in step S903, the apparatus for evaluating validity of detection of the cancer region may receive the image to be analyzed. Here, the image to be analyzed may be MRI obtained by capturing the body of the user (or the patient) to be subjected to cancer diagnosis and may include the above-described at least one parametric MRI.

As the image to be analyzed is input (S902—Yes), the apparatus for evaluating validity of detection of the cancer region may check cancer region information using the diagnosis region detection region and the cancer region detection model (S904).

Specifically, as raw parametric MRI 501, 502 and 503 (see FIG. 5a) is received as the image to be analyzed, the apparatus for evaluating validity of detection of the cancer region may detect and output the parametric MRI 511, 512 and 513 of the diagnosis region using the diagnosis region detection model.

In response to this, the apparatus for evaluating validity of detection of the cancer region may input the parametric MRI 511, 512 and 513 of the diagnosis region to the cancer region detection model and output cancer region information.

In particular, the apparatus for evaluating validity of detection of the cancer region may output an image 271 in which a region 271a (see FIG. 2b) where cancer is located is marked in the parametric MRI 511, 512 and 513 of the diagnosis region, as cancer region information.

In step S905, the apparatus for evaluating validity of detection of the cancer region may generate and provide guide information using the cancer region information checked through step S904.

Specifically, the apparatus for evaluating validity of detection of the cancer region may output the image 271, in which the region where cancer is located is marked, as guide information through a display.

Furthermore, the cancer region detection model may be built through learning that extracts the feature of the image to be analyzed and generates predetermined context information based on the extracted feature, and the context information may be constructed based on a probability value for a feature region included in the image to be analyzed. Based on this, in step S904, the apparatus for evaluating validity of detection of the cancer region may provide, as cancer region information, the probability value for the feature region detected as the cancer region.

In addition, in step S905, the apparatus for evaluating validity of detection of the cancer region may generate guide information using the probability value for the feature region detected as the cancer region. For example, the apparatus for evaluating validity of detection of the cancer region may set a predetermined threshold value, set, as a candidate point, a region in which the probability value for the feature region detected as the cancer region exceeds the predetermined threshold, and construct a guide image 272 including set candidate points 272a, 272b and 272c (see FIG. 2b).

In step S906, the apparatus for evaluating validity of detection of the cancer region may receive the second cancer region based on the guide information. For example, the apparatus for evaluating validity of detection of the cancer region may provide an input interface capable of displaying the guide information and receiving the second cancer region.

For example, the input interface 280 (see FIG. 2b) may include an image display portion 281 for displaying a T2 image, a predetermined indicator 282 output in a region designated by an external input device and a second cancer region indicator 283 for setting and displaying a predetermined region selected through the indicator 282 as a cancer region.

Accordingly, the user (such as the expert or the doctor) may set and input a predetermined region as a second cancer region through the input interface, while checking the guide information (e.g., the guide information 272).

Although, in the embodiment of the present disclosure, a T2 image is displayed by the image display portion 281, the present disclosure does not limit the image displayed by the image display portion 281. The image displayed by the image display portion 281 may be variously changed in correspondence with the diagnosis region or the cancer region.

In step S907, the apparatus for evaluating validity of detection of the cancer region may receive the first cancer region based on the parametric MRI. That is, the apparatus for evaluating validity of detection of the cancer region may provide an input interface for displaying the guide information and receiving the first cancer region.

For example, the apparatus for evaluating validity of detection of the cancer region may provide at least one parametric MRI, such that the user (such as the expert or the doctor) sets the first cancer region while referring to at least one parametric MRI. In addition, the apparatus for evaluating validity of detection of the cancer region may provide a screen 200 including a parametric MRI display portion 210 (see FIG. 2a) for displaying at least one parametric MRI and an input interface 220 capable of inputting the first cancer region.

The parametric MRI display portion 210 may include display portions 211, 212, 213 and 214 for displaying at least one of a T2 image, an ADC image, DWI or DCE signal information.

In addition, the input interface 220 may include an image display portion 221 for displaying a T2 image and a predetermined indicator 222 which may be connected through an external input device such as a mouse device, a digitizer device or a touchscreen device and is output in a region designated by the external input device. In addition, the input interface 220 may set a predetermined region selected through the indicator 222 as a cancer region, and include a first cancer region indicator 223 for displaying the region set as the cancer region.

In such an environment, the user (such as the expert or the doctor) may set and input a predetermined region as the first cancer region through the input interface, while checking at least one parametric MRI.

Although, in the embodiment of the present disclosure, a T2 image is displayed by the image display portion 221, the present disclosure does not limit the image displayed by the image display portion 221. The image displayed by the image display portion 221 may be variously changed in correspondence with the diagnosis region or the cancer region.

Meanwhile, if there is no difference in input time between the first cancer region and the second cancer region, the user (such as the expert or the doctor) may input the first cancer region (or the second cancer region) and then input the second cancer region (or the first cancer region) in a state in which the first cancer region (or the second cancer region) input thereby is recognized. In this way, when the user (such as the expert or the doctor) inputs the second cancer region (or the first cancer region) in a state in which the first cancer region (or the second cancer region) input thereby is recognized, the second cancer region (or the first cancer region) may be input based on the will of the user (such as the expert or the doctor). When the second cancer region (or the first cancer region) is input based on the will of the user (such as the expert or the doctor), the second cancer region (or the first cancer region) may not be accurately input, and it may be difficult to determine validity of the second cancer region (or the first cancer region).

In consideration of the above description, the apparatus for evaluating validity of detection of the cancer region may perform step S907 when a predetermined time (e.g., 1 week or 1 month) has elapsed after step S906 is performed. To this end, the apparatus for evaluating validity of detection of the cancer region may determine whether the predetermined time (e.g., 1 week or 1 month) has elapsed after step S906 is completed, and perform step S907 as the predetermined time (e.g., 1 week or 1 month) has elapsed.

Meanwhile, a portion (e.g., a prostate region) of the body region of the user (or the patient) may be extracted through surgery, and the pathology image showing a region, in which cancer tissues are present, in the extracted body region may be constructed. In consideration of this, the apparatus for evaluating validity of detection of the cancer region may provide an environment capable of receiving a pathology image, and display the received pathology image through a display (S908). For example, the pathology image may include a pathology map of a region, in which cancer tissues are present, of the extracted body region constructed in the form of an image.

In step S909, the apparatus for evaluating validity of detection of the cancer region may generate validity evaluation information of the second cancer region, by comparing the first cancer region with the second cancer region based on the pathology image.

For example, the apparatus for evaluating validity of detection of the cancer region may divide a portion (e.g., a prostate region) of the body region in predetermined size units 302 (see FIG. 3a) and construct the first binary map 304 for a predetermined unit, in which the first cancer region 303 is present, in the region.

In addition, the apparatus for evaluating validity of detection of the cancer region may divide the pathology image 311 in predetermined size units 302 (see FIG. 3a) (312) and construct the pathology binary map 314 for a predetermined unit, in which the first cancer region 313 is present, in the region in which the portion (e.g., the prostate region) of the body region is located.

In addition, the apparatus for evaluating validity of detection of the cancer region may check the first coincidence degree information 320 of the first binary map 304, based on the pathology binary map 314. The first coincidence degree information 320 may be information numerically indicating a degree of similarity between corresponding unit regions of the pathology binary map 314 and the first binary map 304. Further, the first coincidence degree information 320 may include sensitivity information and specificity information of the unit region.

Similarly, the apparatus for evaluating validity of detection of the cancer region may divide a portion (e.g., a prostate region) of the body region in a predetermined size unit 332 (see FIG. 3b), and construct the second binary map 334 for a predetermined unit, in which the second cancer region 333 is present, in the corresponding region. In addition, the apparatus for evaluating validity of detection of the cancer region may check second coincidence degree information 340 of the second binary map 334 based on the pathology binary map 314. The second coincidence degree information 340 may be information numerically indicating a degree of similarity between corresponding unit regions of the pathology binary map 314 and the second binary map 334. Further, the second coincidence degree information 340 may include sensitivity information and specificity information of the unit region.

In addition, the apparatus for evaluating validity of detection of the cancer region may calculate and output validity evaluation information, by comparing the first coincidence degree information 320 with the second coincidence degree information 340 (see FIG. 3c). For example, the apparatus for evaluating validity of detection of the cancer region may compare the first coincidence degree information 320 with the second coincidence degree information 340, determine that the second cancer region is valid when the second coincidence degree information 340 has a relatively higher value than the first coincidence degree information 320, and determine that the second cancer region is not valid when the second coincidence degree information 340 has the same value as or a relatively lower value than the first coincidence degree information 320.

The second cancer region is designated as a region, in which a cancer region is likely to be present, by the user (such as the expert or the doctor) based on the guide information. Accordingly, when the validity evaluation information indicates that the second cancer region is valid, a component for providing the guide information may be recognized as a device which may be effectively used to determine a region where cancer is present.

Figure 10:
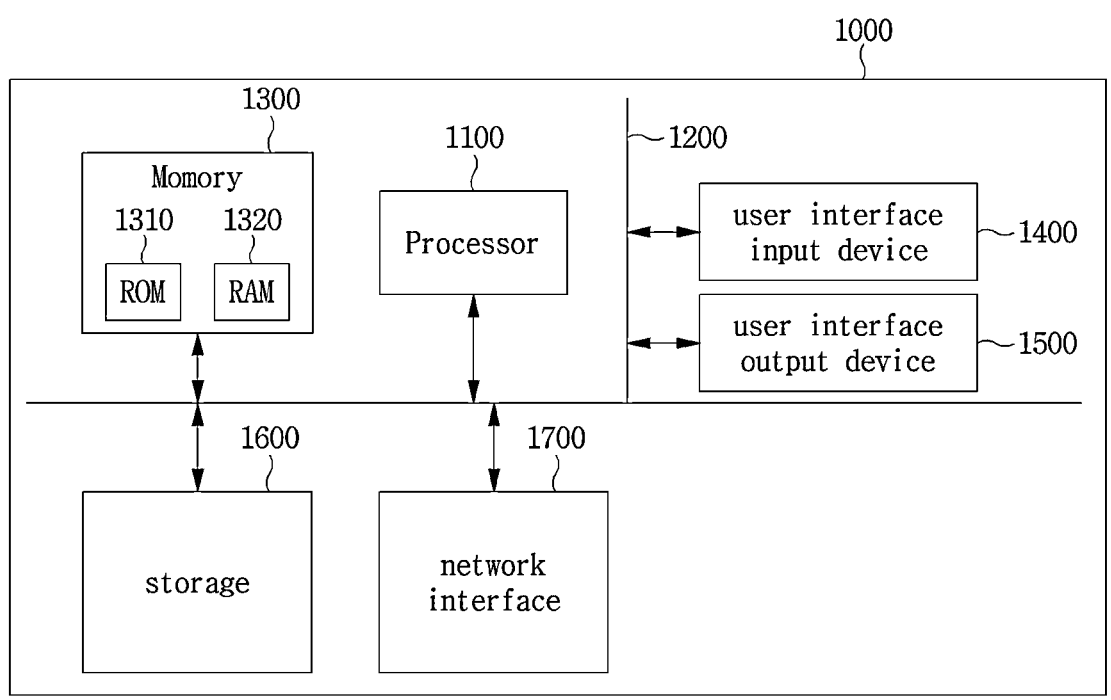
FIG. 10 is a block diagram illustrating a computing system for executing a method and apparatus for evaluating validity of detection of a cancer region according to an embodiment of the present disclosure.

FIG. 10 is a block diagram illustrating a computing system for executing a method and apparatus for evaluating validity of detection of a cancer region according to an embodiment of the present disclosure.

Referring to FIG. 10, a computing system 100 may include at least one processor 1100 connected through a bus 1200, a memory 1300, a user interface input device 1400, a user interface output device 1500, a storage 1600, and a network interface 1700.

The processor 1100 may be a central processing unit or a semiconductor device that processes commands stored in the memory 1300 and/or the storage 1600. The memory 1300 and the storage 1600 may include various volatile or non-volatile storing media. For example, the memory 1300 may include a ROM (Read Only Memory) and a RAM (Random Access Memory).

Accordingly, the steps of the method or algorithm described in relation to the embodiments of the present disclosure may be directly implemented by a hardware module and a software module, which are operated by the processor 1100, or a combination of the modules. The software module may reside in a storing medium (that is, the memory 1300 and/or the storage 1600) such as a RAM memory, a flash memory, a ROM memory, an EPROM memory, an EEPROM memory, a register, a hard disk, a detachable disk, and a CD-ROM. The exemplary storing media are coupled to the processor 1100 and the processor 1100 can read out information from the storing media and write information on the storing media. Alternatively, the storing media may be integrated with the processor 1100. The processor and storing media may reside in an application specific integrated circuit (ASIC). The ASIC may reside in a user terminal. Alternatively, the processor and storing media may reside as individual components in a user terminal.

The exemplary methods described herein were expressed by a series of operations for clear description, but it does not limit the order of performing the steps, and if necessary, the steps may be performed simultaneously or in different orders. In order to achieve the method of the present disclosure, other steps may be added to the exemplary steps, or the other steps except for some steps may be included, or additional other steps except for some steps may be included.

Various embodiments described herein are provided to not arrange all available combinations, but explain a representative aspect of the present disclosure and the configurations about the embodiments may be applied individually or in combinations of at least two of them.

Further, various embodiments of the present disclosure may be implemented by hardware, firmware, software, or combinations thereof. When hardware is used, the hardware may be implemented by at least one of ASICs (Application Specific Integrated Circuits), DSPs (Digital Signal Processors), DSPDs (Digital Signal Processing Devices), PLDs (Programmable Logic Devices), FPGAs (Field Programmable Gate Arrays), a general processor, a controller, a micro controller, and a micro-processor.

The scope of the present disclosure includes software and device-executable commands (for example, an operating system, applications, firmware, programs) that make the method of the various embodiments of the present disclosure executable on a machine or a computer, and non-transitory computer-readable media that keeps the software or commands and can be executed on a device or a computer.

INDUSTRIAL APPLICABILITY

The present disclosure may be utilized in a disease detection field.

The invention claimed is:

1. An apparatus for evaluating validity of detection of a cancer region, the apparatus comprising:
    a parametric magnetic resonance imaging (MRI) provider configured to provide at least one MRI constructed based on different parameters;
    a first cancer region input unit configured to receive a first cancer region based on the at least one parametric MRI;
    a cancer region processor including a cancer region detection model for receiving the at least one parametric MRI as input and outputting cancer region information and configured to generate and provide guide information corresponding to an image to be analyzed through the cancer region detection model;
    a second cancer region input unit configured to receive a second cancer region based on the guide information; and
    a validity evaluator configured to generate validity evaluation information of the second cancer region, by comparing the first cancer region with the second cancer region based on a pathology image obtained by mapping a region, in which cancer is present, of an extracted body portion.

2. The apparatus of claim 1, wherein the validity evaluator checks first coincidence degree information numerically indicating a degree of coincidence, for a predetermined unit of the first cancer region corresponding to a predetermined unit region of the pathology image.

3. The apparatus of claim 2, wherein the validity evaluator checks second coincidence degree information numerically indicating a degree of coincidence, for a predetermined unit of the second cancer region corresponding to a predetermined unit region of the pathology image.

4. The apparatus of claim 3, wherein the validity evaluator generates validity evaluation information by comparing the first coincidence degree information with the second coincidence degree information.

5. The apparatus of claim 2, wherein the first coincidence degree information or the second coincidence degree information comprises sensitivity information and specificity information.

6. The apparatus of claim 1, wherein the cancer region detection model outputs a probability value of presence of cancer for at least one feature region included in the cancer region.

7. The apparatus of claim 1, wherein the at least one parametric MRI comprises at least one of a T1 (T1-weighted) image, a T2 (T2-weighted) image, a T2*(T2 star) image, an apparent diffusion coefficients (ADC) image, a fluid attenuated inversion recovery (FLAIR) image, a short TI inversion recovery (STIR) image or a perfusion weighted image (PWI).

8. The apparatus of claim 1, wherein the cancer region detection model determines the cancer region based on labeling information of the cancer region set using at least one reference information.

9. The apparatus of claim 8, wherein the at least one reference information comprises at least one of a pathology image displayed by imaging a region, in which cancer is present, of an extracted diagnosis region, a Diffusion-weighted imaging (DWI) or dynamic contrast enhanced (DCE) signal information.

10. The apparatus of claim 8, wherein the cancer region detection model comprises:
    a first deep learning model configured to receive the at least one parametric MRI as input and to perform leaning based on information labeling the cancer region based on the at least one parametric MRI;
    a second deep learning model configured to receive the at least one parametric MRI and DWI as input and to perform learning based on information labeling the cancer region based on the at least one parametric MRI and DWI; and
    a third deep learning model configured to receive the at least one MRI and DCE signal information as input and to perform learning based on information labeling the cancer region based on the at least one parametric MRI and DCE signal information.

11. A method of evaluating validity of detection of a cancer region, the method comprising:
    providing at least one parametric magnetic resonance imaging (MRI) constructed based on different parameters;
    receiving a first cancer region based on the at least one parametric MRI;
    building a cancer region detection model for receiving the at least one parametric MRI as input and outputting cancer region information;
    providing guide information corresponding to an image to be analyzed through the cancer region detection model;
    receiving a second cancer region based on the guide information; and
    generating validity evaluation information of the second cancer region by comparing the first cancer region with the second cancer region based on a pathology image obtained by mapping a region, in which cancer is present, of an extracted body portion.

12. The method of claim 11, wherein the generating the validity evaluation information comprises checking first coincidence degree information numerically indicating a degree of coincidence, for a predetermined unit of the first cancer region corresponding to a predetermined unit region of the pathology image.

13. The method of claim 12, wherein the generating the validity evaluation information comprises checking second coincidence degree information numerically indicating a degree of coincidence, for a predetermined unit of the second cancer region corresponding to a predetermined unit region of the pathology image.

14. The method of claim 13, wherein the generating the validity evaluation information comprises generating validity evaluation information by comparing the first coincidence degree information with the second coincidence degree information.

15. The method of claim 12, wherein the first coincidence degree information or the second coincidence degree information comprises sensitivity information and specificity information.

16. The method of claim 11, wherein the cancer region detection model outputs a probability value of presence of cancer for at least one feature region included in the cancer region.

17. The method of claim 11, wherein the at least one parametric MRI comprises at least one of a T1 (T1-weighted) image, a T2 (T2-weighted) image, a T2*(T2 star) image, an apparent diffusion coefficients (ADC) image, a fluid attenuated inversion recovery (FLAIR) image, a short TI inversion recovery (STIR) image or a perfusion weighted image (PWI).

18. The method of claim 11, wherein the cancer region detection model determines the cancer region based on labeling information of the cancer region set using at least one reference information.

19. The method of claim 18, wherein the at least one reference information comprises at least one of a pathology image displayed by imaging a region, in which cancer is present, of an extracted diagnosis region, a Diffusion-weighted imaging (DWI) or dynamic contrast enhanced (DCE) signal information.

20. The method of claim 18, wherein the cancer region detection model comprises:
a first deep learning model configured to receive the at least one parametric MRI as input and to perform leaning based on information labeling the cancer region based on the at least one parametric MRI;
a second deep learning model configured to receive the at least one parametric MRI and DWI as input and to perform leaning based on information labeling the cancer region based on the at least one parametric MRI and DWI; and
a third deep learning model configured to receive the at least one MRI and DCE signal information as input and to perform leaning based on information labeling the cancer region based on the at least one parametric MRI and DCE signal information.

* * * * *